US012558328B2

(12) United States Patent
Zhang et al.

(10) Patent No.: US 12,558,328 B2
(45) Date of Patent: ***Feb. 24, 2026

(54) SOLID-FORMING TOPICAL FORMULATIONS FOR PAIN CONTROL

(71) Applicant: Crescita Therapeutics Inc., Mississauga (CA)

(72) Inventors: Jie Zhang, Salt Lake City, UT (US); Wade Hull, Kaysville, UT (US); Ngoc Truc-Chi Vo, Longueuil (CA)

(73) Assignee: Crescita Therapeutics Inc., Mississauga (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/669,421

(22) Filed: Feb. 11, 2022

(65) Prior Publication Data

US 2022/0160661 A1     May 26, 2022

Related U.S. Application Data

(60) Continuation of application No. 16/929,487, filed on Jul. 15, 2020, now abandoned, which is a division of application No. 15/655,595, filed on Jul. 20, 2017, now Pat. No. 10,751,305, which is a continuation-in-part of application No. 15/613,695, filed on Jun. 5, 2017, now Pat. No. 10,350,180, which is a continuation of application No. 13/006,780, filed on Jan. 14, 2011, now Pat. No. 9,693,976.

(60) Provisional application No. 61/294,927, filed on Jan. 14, 2010.

(51) Int. Cl.
| | |
|---|---|
| *A61K 31/167* | (2006.01) |
| *A61K 9/00* | (2006.01) |
| *A61K 31/136* | (2006.01) |
| *A61K 47/32* | (2006.01) |

(52) U.S. Cl.
CPC .......... *A61K 31/167* (2013.01); *A61K 9/0014* (2013.01); *A61K 31/136* (2013.01); *A61K 47/32* (2013.01)

(58) Field of Classification Search
CPC ... A61K 31/136; A61K 9/0014; A61K 31/167
See application file for complete search history.

(56) References Cited

U.S. PATENT DOCUMENTS

| | | | |
|---|---|---|---|
| 3,929,131 | A | 12/1975 | Hardwick |
| 4,230,105 | A | 10/1980 | Harwood |
| 4,286,592 | A | 9/1981 | Chandrasekaran |
| 4,529,601 | A | 7/1985 | Broberg et al. |
| 4,685,911 | A | 8/1987 | Konno et al. |
| 4,693,706 | A | 9/1987 | Ennis, III |
| 4,695,465 | A | 9/1987 | Kigasawa et al. |
| 4,747,841 | A | 5/1988 | Kuratomi et al. |
| 4,780,320 | A | 10/1988 | Baker |
| 4,830,855 | A | 5/1989 | Stewart |
| 4,879,119 | A | 11/1989 | Konno et al. |
| 4,898,592 | A | 2/1990 | Latzke et al. |
| 4,911,707 | A | 3/1990 | Heiber et al. |
| 4,913,957 | A | 4/1990 | Strack et al. |
| 4,963,360 | A | 10/1990 | Argaud |
| 4,994,049 | A | 2/1991 | Latzke et al. |
| 5,108,710 | A | 4/1992 | Little et al. |
| 5,114,411 | A | 5/1992 | Haber et al. |
| 5,128,137 | A | 7/1992 | Muller et al. |
| 5,147,339 | A | 9/1992 | Sundstrom |
| 5,213,129 | A | 5/1993 | Someah et al. |
| 5,217,718 | A | 6/1993 | Colley et al. |
| 5,229,133 | A | 7/1993 | Wright et al. |
| 5,276,032 | A | 1/1994 | King et al. |
| 5,279,594 | A | 1/1994 | Jackson |
| 5,329,976 | A | 7/1994 | Haber et al. |
| 5,330,452 | A | 7/1994 | Zook |
| 5,364,350 | A | 11/1994 | Dittmann |

(Continued)

FOREIGN PATENT DOCUMENTS

| | | |
|---|---|---|
| DE | 2851369 | 6/1979 |
| EP | 0386960 | 9/1990 |

(Continued)

OTHER PUBLICATIONS

Unknown, Local Anesthetics, https://web.archive.org/web/20120906202800/http://www.ifna-int.org/ifna/e107_files/downloads/lectures/H1LocalAne.pdf, downloaded Aug. 11, 2014, 20 pages.
Unknown, Types of Polymers, https://web.archive.org/web/20070712124323/http://chemed.chem.purdue.edu/genchem/topicreview/bp/1polymer/types.html, downloaded Aug. 12, 2014, 7 pages.
Saupe, Biological Polymers: Proteins, Carbohydrates, Lipids & Nucleic Acids, Introduction to Cell & Molecular Biology(BIOL121), https://web.archive.org/web/20081116091144/http://employees.csbsju.edu/SSAUPE/biol121/chem_biol.html, downloaded Aug. 12, 2014, 4 pages.
Astra USA, Inc., EMLA Cream (lidocaine 2.5% and prilocaine 2.5%), Product Information Form for AmericanHospital Formulary Service, 1993, 27 pages.

(Continued)

*Primary Examiner* — Marcos L Sznaidman

(74) *Attorney, Agent, or Firm* — Thorpe North & Western, LLP

(57) ABSTRACT

Methods of applying a solid forming local anesthetic formulations can include applying a layer of a solid-forming formulation to a skin surface, wherein the solid-forming local anesthetic formulation includes from 4 wt % to 30 wt % of a local anesthetic, less than 36 wt % dicalcium phosphate, water, and a polymer. These methods can further include maintaining the layer of the formulation on the skin surface for a period of time sufficient to allow the layer of the formulation to transition from a semi-solid to a cohesive film and to topically deliver the local anesthetic to the skin surface, and removing the layer of the formulation from the skin surface by peeling the layer of the formulation off the skin surface. The layer of the formulation can be operable to be removed as a single piece or two to three large pieces.

21 Claims, 4 Drawing Sheets

(56) References Cited

U.S. PATENT DOCUMENTS

| | | | |
|---|---|---|---|
| 5,370,879 A | 12/1994 | Masterson et al. | |
| 5,378,730 A | 1/1995 | Lee et al. | |
| 5,658,583 A | 8/1997 | Zhang et al. | |
| 5,733,572 A | 3/1998 | Unger et al. | |
| 5,776,952 A | 7/1998 | Liedtke | |
| 5,840,755 A | 11/1998 | Liedtke | |
| 5,885,597 A | 3/1999 | Botknecht et al. | |
| 5,906,814 A | 5/1999 | Epstein | |
| 5,919,479 A | 7/1999 | Zhang et al. | |
| 5,993,836 A | 11/1999 | Castillo | |
| 6,017,388 A * | 1/2000 | Yuan | C08B 30/12 |
| | | | 426/804 |
| 6,036,966 A | 3/2000 | Youssefyeh | |
| 6,211,250 B1 | 4/2001 | Tomlinson et al. | |
| 6,245,347 B1 | 6/2001 | Zhang et al. | |
| 6,261,595 B1 | 7/2001 | Stanley et al. | |
| 6,324,424 B1 | 11/2001 | Ledger et al. | |
| 6,453,648 B1 | 9/2002 | Zhang | |
| 6,465,709 B1 | 10/2002 | Sun et al. | |
| 6,488,959 B2 | 12/2002 | Stanley et al. | |
| 6,528,086 B2 | 3/2003 | Zhang | |
| 6,756,053 B2 | 6/2004 | Zhang et al. | |
| 6,756,426 B2 | 6/2004 | Brother et al. | |
| 6,955,819 B2 | 10/2005 | Zhang et al. | |
| 7,063,859 B1 | 6/2006 | Kanios et al. | |
| 2002/0004063 A1 * | 1/2002 | Zhang | A61P 15/10 |
| | | | 424/443 |
| 2004/0131665 A1 * | 7/2004 | Wepfer | A61K 31/167 |
| | | | 424/449 |
| 2005/0037080 A1 * | 2/2005 | Lynch | A01M 1/2055 |
| | | | 424/488 |
| 2005/0075407 A1 | 4/2005 | Tamarkin et al. | |
| 2005/0136079 A1 * | 6/2005 | Burangulov | A61K 8/86 |
| | | | 424/125 |
| 2005/0209319 A1 | 9/2005 | Cundy | |
| 2005/0232957 A1 | 10/2005 | Katz | |
| 2005/0239868 A1 | 10/2005 | Shirai et al. | |
| 2005/0276842 A1 | 12/2005 | Zhang et al. | |
| 2006/0067958 A1 * | 3/2006 | Valencia | A61K 9/0014 |
| | | | 424/401 |
| 2006/0147510 A1 | 7/2006 | Galer | |
| 2007/0059351 A1 | 3/2007 | Murrell et al. | |
| 2007/0068508 A1 | 3/2007 | York-Leung Wong | |
| 2007/0189978 A1 | 8/2007 | Zhang | |
| 2007/0196323 A1 * | 8/2007 | Zhang | A61K 9/0014 |
| | | | 424/78.02 |
| 2007/0196458 A1 | 8/2007 | Zhang et al. | |
| 2007/0299540 A1 | 12/2007 | Ku | |
| 2008/0021051 A1 | 1/2008 | Wilson | |
| 2008/0260655 A1 | 10/2008 | Tamarkin et al. | |
| 2010/0273838 A1 | 10/2010 | Cui et al. | |
| 2011/0015229 A1 * | 1/2011 | Zhang | A61K 47/32 |
| | | | 514/626 |

FOREIGN PATENT DOCUMENTS

| | | |
|---|---|---|
| EP | 0455396 | 11/1991 |
| EP | 0770387 | 5/1997 |
| EP | 2163956 | 3/2010 |
| GB | 2163959 | 3/1986 |
| JP | 62051617 | 3/1987 |
| JP | 5279018 | 10/1993 |
| WO | WO8809169 | 12/1988 |
| WO | WO9213529 | 8/1992 |
| WO | WO9619453 | 6/1996 |
| WO | WO9715548 | 5/1997 |
| WO | WO9738675 | 10/1997 |
| WO | WO9922717 | 5/1999 |
| WO | WO0018339 | 4/2000 |
| WO | WO0122907 | 4/2001 |
| WO | WO2004000358 | 12/2003 |
| WO | WO2005120473 | 12/2005 |
| WO | WO2007070679 | 6/2007 |
| WO | WO2008150995 | 12/2008 |
| WO | WO2009053572 | 4/2009 |
| WO | WO2010080831 | 7/2010 |
| WO | WO2010114973 | 10/2010 |
| WO | WO2010129542 | 11/2010 |
| WO | WO2011088333 | 7/2011 |
| WO | WO2012080831 | 6/2012 |

OTHER PUBLICATIONS

Cada et al., Lidocaine/Tetracaine Patch, Formulary Drug Reviews, Hospital Pharmacy, vol. 41, No. 3, 2006 WoltersKluwer Health, Inc., pp. 265-273.

Hoshino et al., Preparation of a Local Anaesthetic Ointment Containing the Eutectic Mixture of Lidocaine andTetracaine, Yakuzalgaku, 1991, abstract only.

Kawano et al., Comparison of analgesic effect of lidocaine tape versus eutectic mixture of lidocaine and tetracaineduring infiltration of local anesthetics before epidural block, PubMed, 1996, abstract only.

Knutson et al., Solvent-Medicated Alterations of the Stratum Corneum, Journal of Controlled Release, 11, 1990, pp. 93-103.

Lycka, EMLA A New and Effective Topical Anesthetic, J Dermatol Sug Oncol, 1992, pp. 859-862.

Mack Publishing Company, Stability of Pharmaceutical Products, 1985, pp. 1481-1482.

Mccafferty et al., Comparative In Vivo and In Vitro Assessment of the Percutaneous Absorption of LocalAnaesthetics, Br. J. Anaesth., 1988, p. 64-69.

Mccafferty et al., In Vivo Assessment of Percutaneous Local Anaesthetic Preparations, Br. J. Anaesth, 1989, pp. 17-21.

Mccafferty et al., New Patch Delivery System for Percutaneous Local Anaesthesia, British Journal of Anaesthesia, 1993, pp. 370-374.

Ohzeki et al., Local Anesthetic Cream Prepared from Lidocaine-Tetracaine Eutectic Mixture, Yakugaku Zasshi 128(4), 2008, pp. 611-616.

Risovic et al., Formulacija I Ispitivanje Rubefacijentnog Dejstva Preparata Sa Kapsaicinom, Lek. Sirov, vol. XXI, No. 21, 2001, pp. 157-161.

Sakamoto et al., Dermal patch anaesthesia: comparison of 10% lignocaine gel with absorption promotor and EMLAcream, Anaesthesia, vol. 48, 1993, pp. 390-392.

Woolfson et al., Concentration-Response Analysis of Percutaneous Local Anaesthetic Formulations, Br. J.Anaesth., vol. 61, 1988, pp. 589-592.

Woolfson, Percutaneous Local Anaesthesia, Formulation of local anaesthetics for percutaneous deliver, Ch. 5,1993, pp. 166-170.

Yap, Myofascial Pain—An Overview, Annals Academy of Medicine, vol. 36, No. 1, 2007, pp. 43-48.

Young, What's New in Topical Anesthesia, Clinical Pediatric Emergency Medicine, 2007, pp. 232-239.

Argoff, A Review of the Use of Topical Analgesics for Myofascial Pain, Current Pain and Headach Reports, 2002, pp. 375-378.

International Search Report and Written Opinion dated Sep. 28, 2011 for PCT/US2011/021318, Applicant Zarspharma, Inc. et al.

European Search Report dated Jun. 7, 2013 for PCT/US2011/021318, Applicant Nuvo Research Inc.

* cited by examiner

SOLID-FORMING TOPICAL FORMULATIONS FOR PAIN CONTROL

This application is Continuation Application of U.S. patent application Ser. No. 16/929,487, filed on Jul. 15, 2020, which is a Divisional Application of U.S. patent application Ser. No. 15/655,595, filed Jul. 20, 2017 and issued as U.S. patent Ser. No. 10/751,305 on Aug. 25, 2020, which is a Continuation-in-part Application of U.S. patent application Ser. No. 15/613,695, filed Jun. 5, 2017 and issued as U.S. Pat. No. 10,350,180 on Jul. 16, 2019, which is a Continuation Application of U.S. Non-provisional patent application Ser. No. 13/006,780, filed Jan. 14, 2011 and issued as U.S. Pat. No. 9,693,976 on Jul. 4, 2017, which claims the benefit of U.S. Provisional Patent Application No. 61/294,927, filed on Jan. 14, 2010, each of which is incorporated herein by reference.

BACKGROUND

Non-invasive pain control methods are desirable in preventing and/or treating pain. It would be useful to provide formulations that have good storage stability, particularly freeze-thaw storage stability, and are effective for pain prevention and treatment. Topical formulations that are easy to apply, dry quickly, and are easy to remove are useful.

DETAILED DESCRIPTION

Figure 1:
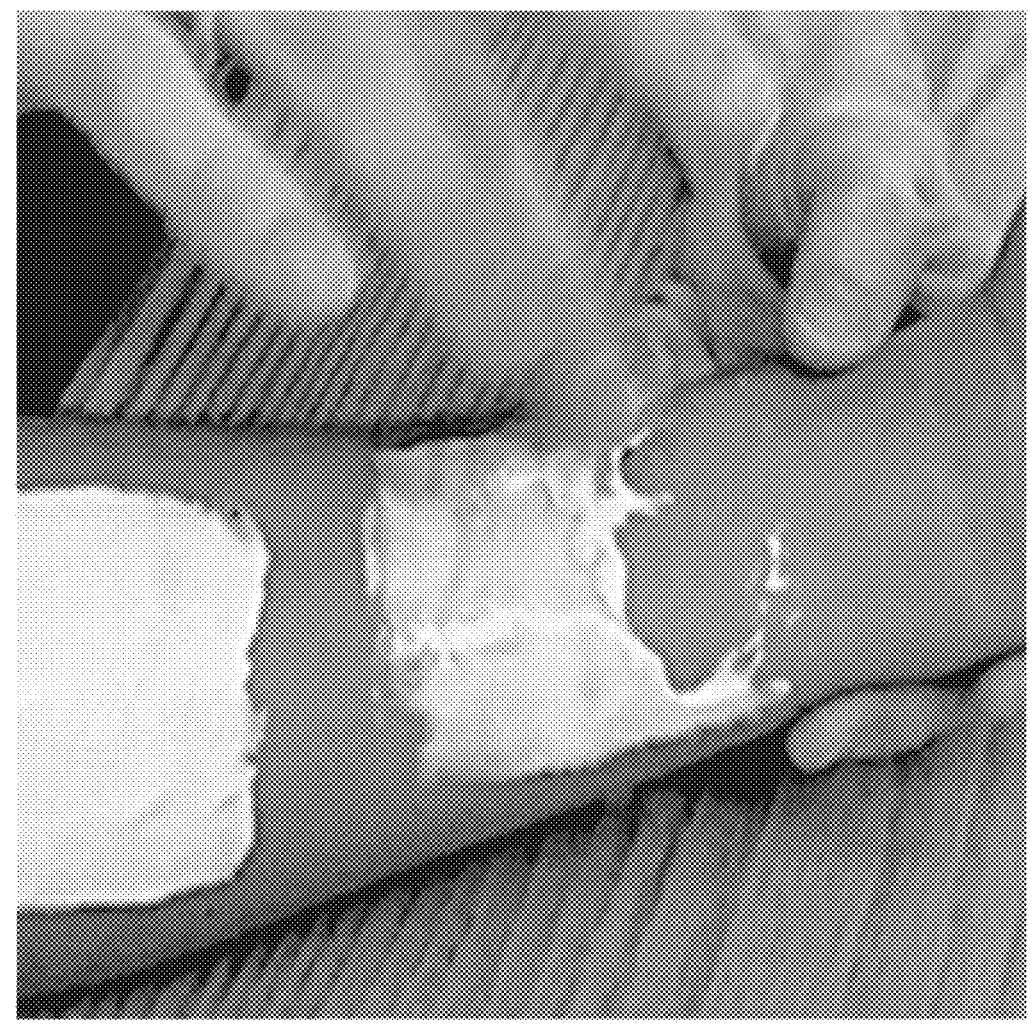
FIG. 1 pictorially illustrates the removal of a 2.5 g dose of Formulation 13 applied on the forearm of a test subject in accordance with an example of the present disclosure.

Before particular embodiments of the present invention are disclosed and described, it is to be understood that this disclosure is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used.

"Skin" is defined to include human skin (intact, diseased, ulcerous, or broken), and mucosal surfaces that are usually at least partially exposed to air such as lips, genital and anal mucosa, and nasal and oral mucosa.

The term "solid-forming topical formulation" or "solid-forming formulation" refers to a formulation that is in the state of a semi-solid and comprises a local anesthetic, water, and a polymer before being applied onto a skin surface. After being applied to a skin surface as a thin layer (e.g., 1 mm thick), the solid-forming topical formulation forms a cohesive film after a sufficient amount of water is evaporated from the formulation layer. Examples of semi-solid forms include creams, ointments, pastes, viscous lotions, gels, and the like. It is notable that the solid-forming formulations of the present disclosure are free of backing layers or backing films and are formulated to be applied directly to a skin surface as a semi-solid state without the need of a separate support substrate (e.g. backing layer or backing film) both before application and after being applied. The ability of the formulation to be applied directly to the skin without a backing layer, backing film, or other support substrate enhances the ability of the formulation to better adhere to regions of a subject's skin that do not readily lend themselves to traditional transdermal patches (i.e. those that include backing layers or backing films). It is further notable that the solid-forming formulations of the present disclosure form a layer of a cohesive film under ambient conditions without further treatment, e.g., without the use of ultraviolet light, conversion agents, heating the skin surface, etc. By enhancing adherence to such surfaces, the solid-forming formulations are more effective in delivering therapeutically effective amounts of the local anesthetics, thereby providing enhanced prevention and/or relief of pain.

As used herein, the term "semi-solid" refers to a composition having a viscosity of about 40,000 centipoise to about 800,000 centipoise. As discussed above, compositions having viscosities in this range that can be deemed semi-solids can include creams, ointments, pastes, viscous lotions, gels, and the like. It is notable that not all of the foregoing compositions are considered to be semi-solids, but rather only those that having viscosities that fall within the above range. In one aspect of the disclosure, the semi-solid formulations can have a viscosity of about 70,000 centipoise to about 500,000 centipoise.

The phrase "sufficient amount of water" refers to an amount of water evaporated from an applied layer of the formulation such that the formulation transitions from a semi-solid to a cohesive film. The amount of time it takes for a sufficient amount of water to evaporate from the applied layer can vary based on the temperature and average humidity as well as a thickness of the applied layer.

The terms "cohesive film" "cohesive solid," or "cohesive soft solid" describe the solidified layer of the solid-forming topical formulation after a sufficient amount of water has evaporated (sufficient to cause the solidification). For simplicity herein, the term "cohesive film" is generally used throughout to describe the formulations described herein after solidification, such as on a skin surface. The cohesive film can remain adhered to the skin and is capable of maintaining good contact with the subject's skin for substantially the entire duration of desired application. Additionally, a "cohesive film" can have cohesive strength sufficient such that the solid remains intact when peeled from the skin. In other words, cohesive films do not include dried lotions and other viscous semi-solids that are non-cohesive even after drying, but rather, include compositions that remain at least partially cohesive in the solid state even after being removed from a skin surface. In one embodiment, the cohesive film can be peelable from the skin, e.g., the cohesive film can remain as a single large piece when peeled from the skin, or tears into two or three large pieces.

The term "initial state" when used to describe a solid-forming topical formulation refers to the state of the formulation before being applied to a skin surface. The state of application in the initial state is typically a semi-solid state, e.g., cream, paste, gel, lotion, ointment, liquid, etc., and not the cohesive film state, e.g., peelable or otherwise removable solid that is coherent as a thin solid layer.

The term "initial viscosity" refers to the viscosity of the formulation at room temperature (typically about 25° C.) and ambient relative humidity (typically about 38-45%) prior to a freeze/thaw cycle.

The term "freeze/thaw cycle" refers to the placement of the formulation in an environment having a temperature of −18° C. to −22° C. for a period of time of about 48 hours followed by the thawing of the formulation at room temperature (a temperature of about 25° C.) for a period of about 48 hours. One freezing and one thawing period together are considered to be one (1) freeze/thaw cycle. It is noted that the temperature range reflects temperature fluctuation associated with the typical cycling of a freezer set to freeze at about −20° C.

The term "pain" refers to any and all types of pain regardless of the cause. The pain may be an existing pain or expected pain to be prevented, e.g., associated with a dermatological procedure. The pain can be acute or chronic. Examples of specific sources of pain for which the methods of the present disclosure can be used include pain associated with superficial dermatological procedures, dermal filler injection, pulsed dye laser therapy, facial laser resurfacing, laser-assisted tattoo removal, laser hair removal, diabetic neuropathies, virus-caused neuropathies, inflammatory pain and the like.

The term "proximate" when referring to an existing pain is a location on a skin surface, particularly as it relates to the location of the existing pain, means an area of skin directly over (in part or fully covering) or immediately adjacent to tissue from which the pain is present.

The term "subject" as used herein includes all members of the animal kingdom, including mammals, and most typically, refers to humans.

As used herein, a plurality of drugs, compounds, and/or solvents may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to about 2.0" should be interpreted to include not only the explicitly recited values of about 0.01 to about 2.0, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. Furthermore, such an interpretation should apply regardless of the breadth of the range or the characteristics being described. Additionally, it is noted that all percentages are in wt/wt, unless specified otherwise.

As used herein the term "topical formulation" refers to a formulation that may be applied to skin. Topical formulations may, for example, be used to confer therapeutic benefit to a subject. Topical formulations can be used for both topical and transdermal administration of substances.

As used herein, the term "transdermal" means in the broadest sense into or through the skin. Transdermal administration is often applied where systemic delivery of an active is desired, although it may also be useful for delivering an active to tissues underlying the skin with minimal systemic absorption (i.e. localized delivery).

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms, such as pain. In addition to being useful as methods of treatment, the methods described herein may be useful for the prevention or prophylaxis of pain.

As used herein, "drying time" refers to a period of time that ranges from the application of the topical formulation to when the applied formulation is dry to the touch. In some aspects, the application and dry time can occur under "ambient conditions," which can be defined as room temperature (22° C. to 23° C.) and relative humidity (38% to 45%).

The term "drying rate" means the rate at which a formulation dries. A first formulation with a shorter drying time is understood to have a "faster drying time" or to "dry faster" than a second formulation with a longer drying time. In this situation, if the first formulation is said to dry X times faster than the second formulation it is to be understood to mean that the drying time for the second formulation is X times longer than the drying time of the first formulation.

In this application, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open-ended term in this written description, like "comprising" or "including," it is understood that direct support should be afforded also to "consisting essentially of" language as well as "consisting of" language as if stated explicitly and vice versa.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. For example, in one embodiment, the degree of flexibility can be within about +−0.5% of the numerical value. In another embodiment, the degree of flexibility can be within about +−0.2% of the numerical value. In a further embodiment, the degree of flexibility can be within about +/−0.1%, or +/−0.05%, of the numerical value. In other examples, when the term "about" is used, removal of the term "about" to leave an exact value is also included within the scope of the present disclosure.

The singular forms "a" "an," and "the" include plural referents unless the context clearly dictates otherwise. Thus, for example, reference to "an anesthetic" includes reference to one or more of such anesthetics.

With this background in mind, a solid-forming topical formulation is provided. In one embodiment, the formulation includes a local anesthetic, an emulsifying agent, a polymer, and water. The formulation can include from 0.1 wt % to 5 wt % more of emulsifying agent, from 0.1 wt % to 20 wt % more of polymer, and from 0.1 wt % to 30 wt % more of water than a comparative formulation, and further can dry faster than the comparative formulation when applied to a skin surface and dried under the same conditions. The comparative formulation can include 7 wt % lidocaine, 7 wt % tetracaine, 2 wt % emulsifying agent, 12 wt % polymer, and about 26 wt % water.

In another embodiment, a method for preventing pain is presented. The method can include applying a layer of the solid-forming topical formulation to a skin surface of a subject and maintaining the layer on the skin surface for a period of time sufficient to allow for delivery of the local anesthetic to the subject, thereby numbing the skin surface.

In yet another embodiment, a method of treating existing pain is provided. The method can include applying a layer of the solid-forming topical formulation to a skin surface of a subject and maintaining the layer on the skin surface for a period of time sufficient to allow for delivery of the local anesthetic to the subject, thereby reducing the pain.

In a further embodiment, a solid-forming topical formulation is provided. This formulation can include lidocaine, tetracaine, an emulsifying agent, polyvinyl alcohol, and water. The solid-forming topical formulation can form a cohesive film that can be removed as one large piece or two or three large pieces.

In another embodiment, a method of preventing pain in a subject prior to a dermatological procedure is provided. The method can include applying a layer of a solid-forming topical formulation including from 4 wt % to 30 wt % of a local anesthetic to a treatment site of a subject and maintaining the layer of the formulation on the treatment site for a period of time sufficient to allow the layer of the formulation to transition from a semi-solid to a cohesive film as well as to topically deliver the local anesthetic to the treatment site of the subject. An additional step can include removing the layer of the formulation from the treatment site of the subject by peeling the layer of the formulation off the treatment site. The layer of the formulation (e.g., as a cohesive film) can have a consistency such that it is removable as a single piece or two to three large pieces and does not leave a residue on a surface of the treatment site. In some embodiments the film is removable in more than three large pieces but the average area of such pieces is greater than about 15 cm². In one example, the formulation can dry at least 1.10 times faster, or at least 1.25 times faster, than a comparative formulation. The comparative formulation can include 7 wt % lidocaine, 7 wt % tetracaine, 2 wt % emulsifying agent, 12 wt % polymer and about 26 wt % water.

In yet another embodiment, a method of treating existing pain in a subject is provided. The method can include applying a layer of a solid-forming topical formulation including from 4 wt % to 30 wt % of a local anesthetic to a skin surface of a subject and maintaining the layer of the formulation on the skin surface for a period of time sufficient to allow the layer of the formulation to transition from a semi-solid to a cohesive film and to topically and/or transdermally deliver the local anesthetic to the subject. An additional step can include removing the layer of the formulation from the skin surface of the subject by peeling the layer of the formulation off the skin surface. The layer of the formulation (e.g., as a cohesive film) can be removable as a as a single piece or as two to three large pieces. The layer of the solid-forming topical formulation can exclude a backing layer, a backing film, or other support substrate. Furthermore, the layer can transition from a semi-solid to a cohesive film. The formulation can dry at least 1.10 times faster, or at least 1.25 times faster, than a comparative formulation with less water. The comparative formulation can include 7 wt % lidocaine, 7 wt % tetracaine, 2 wt % emulsifying agent, 12 wt % polymer, and about 26 wt % water.

In another embodiment, a formulation for providing pain control can include lidocaine and tetracaine each in their base forms, polyvinyl alcohol, and water. The formulation can have an initial viscosity of about 40,000 centipoise to about 800,000 centipoise at approximately room temperature, and can have an increase in viscosity after 3 freeze/thaw cycles of less than 8 times the initial viscosity with a maximum viscosity of 1,500,000 centipoise at approximately room temperature. Each of the 3 freeze/thaw cycles can be determined by placement of the formulation in an environment of −18° C. to −22° C. for a period of time of 48 hours followed by the thawing of the formulation at room temperature (about 25° C.) for a period of 48 hours.

In still another embodiment, a formulation for providing pain control can include from 4 wt % to 30 wt % of a eutectic mixture of lidocaine and tetracaine, from 10 wt % to 18 wt % polyvinyl alcohol, from 30 wt % to 50 wt % water, from 2 wt % to 13 wt % petrolatum, and from 2 wt % to 6 wt % sorbitan monostearate. The water to polyvinyl alcohol weight ratio can be greater than 2.4. Also, the formulation can have an initial viscosity of about 70,000 centipoise to about 500,000 centipoise at approximately room temperature, and can have an increase in viscosity after 3 freeze/thaw cycles of less than 8 times the initial viscosity with a maximum viscosity of 1,500,000 centipoise at approximately room temperature. Each of the 3 freeze/thaw cycles can be determined by placement of the formulation in an environment of −18° C. to −22° C. for a period of time of 48 hours followed by the thawing of the formulation at room temperature (about 25° C.) for a period of 48 hours.

In another embodiment, a method of applying a solid forming local anesthetic formulation can include applying a layer of a solid-forming formulation to a skin surface where the solid-forming local anesthetic formulation includes from 4 wt % to 30 wt % of a local anesthetic, less than 36 wt % dicalcium phosphate, water, and a polymer. The method can also include maintaining the layer of the formulation on the skin surface for a period of time sufficient to allow the layer of the formulation to transition from a semi-solid to a cohesive film and to topically deliver the local anesthetic to the skin surface, and removing the layer of the formulation from the skin surface by peeling the layer of the formulation off the skin surface, wherein the layer of the formulation is operable to be removed as a single piece or two to three large pieces.

It is noted that when discussing the various formulations and methods described herein, each of these discussions can be considered applicable to the other examples, whether or not they are explicitly discussed in the context of that example. Thus, for example, in discussing a local anesthetic related to a formulation, such disclosure is also relevant to and directly supported in the context of any of the methods described herein, other formulations described herein, and vice versa.

The solid forming topical formulations in the present disclosure can include a variety of local anesthetics. Non-limiting examples of local anesthetics can include lidocaine, tetracaine, bupivacaine, ropivacaine, prilocaine, etidocaine, benzocaine, or combinations thereof. In one example, the local anesthetic in the formulations can be a mixture of lidocaine and tetracaine. The local anesthetic can be included in their base form. In one example, the local anesthetic can be a eutectic mixture of multiple local anesthetics where each local anesthetic is in its base form.

The local anesthetic can be present in total within the composition as a whole at from about 4 wt % to about 30 wt %, in one example. In other examples, the local anesthetic can appear in the formulation at from about 8 wt % to about 20 wt %, from about 10 wt % to about 18 wt %, or from about 6 wt % to about 16 wt %. In one example, the formulation can include lidocaine and tetracaine in a mixture, at about 7 wt % each. In yet other examples, each of these two local anesthetics can be present at about 5 wt %, about 6 wt %, about 8 wt %, or about 10 wt %. In some examples, the mixture can include local anesthetics in their base form and/or can be a eutectic mixture of local anesthetics. For example, a mixture of lidocaine and tetracaine at a 1:1 weight ratio, each in their base form, can create a eutectic mixture of lidocaine and tetracaine.

If two local anesthetics are used in combination, any functional ratio of local anesthetics can be present. In one example, however, a base weight ratio of two local anesthetics can range from 2:1 to 1:2, and can often be about 1:1. For example, a weight ratio of lidocaine to tetracaine can range from 2:1 to 1:2, and in another example, the weight ratio lidocaine to tetracaine can be 1:1.

The formulations presented herein can include an emulsifying agent. Exemplary emulsifying agents can include gelatin, lecithin, sorbitan esters (sold under the trade name Span® (Atlas Powder Company)), polysorbates, poly oxyethylene, fatty acid esters, polymeric emulsifiers (e.g. Pemulen™ TR-1, Pemulen™ TR-2 (Lubrizol Advanced Materials, Inc.), and the like), and combinations thereof. In one example the emulsifying agent can be selected from sorbitan monopalmitate (Span® 40), sorbitan monostearate (Span® 60), or combinations thereof. In one example, the emulsifying agent can be sorbitan monostearate. In another example, the emulsifying agent can be sorbitan monopalmitate. In some examples, the emulsifying agent can be present in the formulation from about 1 wt % to about 15% wt, or from about 3 wt % to about 15 wt %. In further examples, the emulsifying agent can be present in the formulation from about 3 wt % to about 10 wt %. In other examples the emulsifying agent can be present up to about 8 wt %, from about 3 wt % to about 8 wt %, or from about 4 wt % to about 6 wt %.

The formulations of the present disclosure can be considered oil-in-water type emulsions, but in some examples, can comprise two or more discontinuous oil phases, with a continuous aqueous phase. More complex forms of emulsions are also herein contemplated, for example, emulsions that include solid particles in one or more phases of the formulation. The emulsifying agent(s) can emulsify the phases of the formulations. For example, in one embodiment, the formulations of the present disclosure can contain two oil phases: a mixture of local anesthetics, e.g. eutectic mixture of lidocaine and tetracaine, and an emollient, e.g., petrolatum. The emulsifying agent can act, in some instances, to combine and stabilize these two oil phases. In other embodiments, the formulation may comprise a single oil phase containing a mixture of anesthetics (e.g. eutectic mixture of lidocaine and tetracaine) and an aqueous phase. Without being bound by theory, the emulsifying agent can act to hold the oil and aqueous phases together.

The formulations presented herein can include a polymer. In one example, the polymer can be polyvinyl alcohol, polyvinyl pyrrolidone, ethyl cellulose, or combinations thereof. In one example, the polymer can be polyvinyl alcohol. The polymer can facilitate the transition of the formulation from an initial semi-solid state to a solidified state, e.g., a cohesive film. Accordingly, it is desirable for the formulations to contain concentrations of polymer sufficient to facilitate this conversion. Formulations with excessive polymer concentrations can have high viscosities and may be too difficult to apply or spread onto a skin surface. Similarly, formulations with insufficient polymer concentrations can produce undesirably long drying times and/or poor cohesion of the solidified layer. Accordingly, in one aspect of the present disclosure, the formulation can include from about 6 wt % to 25 wt % polymer. In other examples, the polymer can be present from about 13 wt % to about 25 wt %, from about 13 wt % to about 18 wt %, from about 13 wt % to about 20 wt %, from about 13 wt % to about 15 wt %, from about 10 wt % to about 18 wt %, or less than or equal to 20 wt %.

In one embodiment, the formulation can include from 0.1 wt % to 5 wt % more of emulsifying agent, from 0.1 wt % to 20 wt % more of polymer, and from 0.1 wt % to 30 wt % more of water than a comparative formulation. In another embodiment, the formulation can include from about 0.1 wt % to about 2.2 wt % more of emulsifying agent, from about 0.1 wt % to about 16.5 wt % more of polymer, and from about 0.1 wt % to 29 wt % more of water than a comparative formulation.

The molecular mass of polymer in the formulation is also notable. Used within the concentration ranges described herein, the polymer's average molecular mass can be in the range of 20,000 to 100,000 Daltons. More typically, the average molecular mass can be in the range of 30,000 to 80,000 Daltons. When lower molecular mass polymers are used, e.g., less than 20,000 Daltons, the viscosity of the formulations can be too low for spreading on the skin and the cohesion can be too weak to provide appropriate adherence to the skin. When polymers with meaningfully higher molecular masses are used, e.g., greater than 100,000 Daltons, the viscosity of the formulations can be too high and the manufacturing of the formulations in large scale can be difficult (higher molecular mass polymers can also be more difficult to dissolve). In one specific example, the average molecular mass of polymers used in the formulations of the examples herein can be in the range of 40,000 to 70,000 Daltons.

The solid-forming topical formulations of the present disclosure can also include water. As mentioned, these formulations are in an initial semi-solid state before they are applied to a skin surface and following application, the formulation forms a soft cohesive film upon evaporation of sufficient amount of water to leave the cohesive film layer behind on the skin surface. The solid-forming topical formulation can deliver the local anesthetics to the skin and underlying tissues from the moment it is applied on the skin surface until substantially all the water is evaporated from the formulation. The term "substantially all" as it relates to water evaporation is understood to mean an amount of water such that at least 95% w/w, or at least 99% w/w, or more of the water has been evaporated. Often, a soft cohesive film forms prior to substantially all of the water being evaporated. After evaporation of substantially all of the water, delivery of the local anesthetics typically stops or slows significantly, although the therapeutic effect may still be present long after the drug delivery has stopped due to the storage of the local anesthetic agents in the skin, and in some cases, because of the mechanical protection to the skin provided by the cohesive film remaining on the skin surface.

The amount of water in the formulations is a significant factor in drug delivery with the formulations of the present disclosure. Formulations with too little water may not deliver enough of the local anesthetic. Formulations with too much water will slide off the skin surface and may not form a cohesive film layer within a feasible or clinically useful amount of time. In one example, the formulation can include at least 30.94 wt % water. In another example, the formulation can include at least 35.94%. In other examples, the formulation can include from about 30 wt % to about 55 wt % water. In other examples, the formulation can include from about 30.94 wt % to about 55 wt %, from about 31.94 wt % to about 55 wt %, from about 35 wt % to about 50 wt %, from about 31.94 wt % to about 40 wt %, or from about 30.94 wt % to about 40 wt % water.

In further detail, due to the presence of the water and other ingredients, the formulations herein start out as a semi-solid. After being applied as a thin layer (e.g., 0.1 mm to 3 mm, from 0.3 mm to 1 mm, etc.), the surface can dry to the touch in about 5-40 minutes, e.g., surface becomes dry enough to touch without damaging the solidifying formulation. Furthermore, given enough time (depending on the formulation ingredients, application thickness, ambient conditions, etc.) the layer can solidify into a cohesive film throughout.

As set forth herein, the formulations of the present disclosure can have initial viscosities of about 40,000 centipoise to about 800,000 centipoise. In one embodiment, the formulation can have a viscosity of about 70000 centipoise to about 500,000 centipoise. These viscosities can allow for the formulations to be readily spread onto skin surfaces without running off. Further, it has been discovered that the formulations of the present disclosure have the unique ability to maintain their viscosities in these ranges after multiple freeze/thaw cycles. This ability provides a significant advantage over previous formulations.

Formulations containing certain polymers, such as polyvinyl alcohol (PVA), and water can experience dramatic increases in viscosity after freeze/thaw cycles. Without being limited by theory, it is believed that the increase in viscosity in these polymer (e.g., PVA) and water containing formulations can be due to the tendency of the PVA to cross-link as a result of these cycles. This increase in viscosity is particularly problematic for consumers and practitioners who store the formulations in refrigerators to comply with the storage recommendations. As the viscosity of the formulations increases, the formulations become increasingly difficult to expel or remove from their storage containers and to apply and spread onto the skin surface, resulting in unusable and wasted formulations. Because refrigerators in the physicians' offices often reach freezing temperatures (below 0° C.), it is desirable that the formulation can experience freeze/thaw cycles without overly significant increases in viscosity.

Accordingly in one example of the present disclosure, the formulations presented herein can have an initial viscosity ranging from about 40,000 centipoise to about 800,000 centipoise and can have an increase in viscosity after at least 3 freeze/thaw cycles of less than eight (8) times the initial viscosity. In another example, the increase in viscosity can be less than five (5) times the initial viscosity. In a further example, the increase in viscosity can be less than three (3) times the initial viscosity. In another example, the formulations can have an initial viscosity from about 70,000 centipoise to about 500,000 centipoise and can have an increase in viscosity after at least 3 freeze/thaw cycles of less than five (5) times the initial viscosity. In yet another example, the formulations can have an initial viscosity from about 70,000 centipoise to about 500,000 centipoise and can have an increase in viscosity after at least 3 freeze/thaw cycles of less than three (3) times the initial viscosity. In a further example, the formulations of the present disclosure can have an initial viscosity from about 70,000 centipoise to about 500,000 centipoise and can have an increase in viscosity after at least 4 freeze/thaw cycles of less than three (3) times the initial viscosity with a maximum viscosity of 1,500,000 centipoise.

In each of these examples, after the prescribed number of freeze-thaw cycles, in one embodiment, the maximum viscosity can remain below a maximum viscosity of 1,500,000 centipoise, regardless of the starting viscosity and the increase in viscosity multiplier, e.g., 8 times, 5 times, 3 times, etc. In other examples, the maximum viscosity of the formulation after the prescribed number of freeze/thaw cycles may not exceed 1,000,000 centipoise, may not exceed 800,000 centipoise, or may not exceed 500,000 centipoise. Unless otherwise specified, all viscosity values in the current disclosure are generated by the viscosity measurement methodology set forth in Example 1. It is noted that in many examples, it may not be desirable to exceed 1,500,000 centipoise (and more particularly, it may not be desirable to exceed 1,000,000 centipoise, or even less) after going through various freeze/thaw cycles because the composition can become difficult to remove from a squeeze tube and apply to a skin surface as a semi-solid after the viscosity gets above 1,500,000 centipoise. When practitioners refrigerate these formulations, if the formulation becomes inadvertently frozen, it can cause the viscosity of the semi-solid formulation to increase as a result of cross-linking between the polymer and the water in the composition and the composition can become virtually unusable. Thus, acceptable freeze/thaw performance as described herein represents a significant advancement in the art as it relates to the specific types of compositions described herein.

Another unique parameter of the formulations of the present disclosure relates to the weight ratio of water to polymer in the formulation (e.g., water to PVA weight ratio). For example, formulations having water to PVA ratios above 2.4 have significantly better freeze-thaw performance than those with water to PVA weight ratio below that threshold. Accordingly, in one example, the formulations of the present disclosure can have a water to PVA ratio (weight/weight or w/w/) of at least 2.4. In another example, the formulations can have a water to PVA ratio (w/w) of at least 2.5. In yet a further example, the formulation can have a water to PVA ratio (w/w) of at least 2.8.

In further examples, the formulations presented herein can include an emollient. A non-limiting list of emollients which may be used in accordance with the present disclosure can include almond oil, aluminum stearate, canola oil, castor oil, ceratonia extract, cetostearyl alcohol, cetyl alcohol, cetyl esters wax, cholesterol, coconut oil, cottonseed oil, cyclomethicone, dibutyl sebacate, dimethicone, ethylene glycol palmitostearate, glycerin, glycerin monostearate, glycerin monooleate, glyceryl monostearate, isopropyl myristate, isopropyl palmitate, lanolin, lecithin, light mineral oil, medium-chain triglycerides, mineral oil, lanolin alcohols, myristyl alcohol, octyldodecanol, oleyl alcohol, petrolatum, safflower glycerides, safflower oil, soybean oil, stearyl alcohol, sunflower oil, tricaprylin, triolein, xylitol, and/or zinc acetate. In one example, the emollient can include white petrolatum. In another example, the emollient can be present at 10 wt % or less in the formulation. In other examples, the emollient can be present at from about 1 wt % to about 10 wt %, at from about 3 wt % to about 8 wt %, or at from about 2 wt % to about 6 wt %.

In yet other examples, the formulations presented herein can include a filler. A non-limiting list of fillers which may be used in accordance with the present invention include ammonium alginate, calcium carbonate, calcium lactate, calcium phosphate dibasic anhydrous, calcium phosphate dibasic dihydrate, calcium phosphate tribasic, calcium silicate, calcium sulfate, cellulose, cellulose acetate, corn starch, pregelatinized starch, dextrates, dextrin, dextrose, erythritol, ethylcellulose, fructose, fumaric acid, glyceryl palmitostearate, lactose, isomalt, kaolin, lactitol, magnesium carbonate, magnesium oxide, maltodextrin, maltose, mannitol, medium-chain triglycerides, polydextrose, polymethacrylates, simethicone, sodium alginate, sodium chloride, sorbitol, starch, sucrose, sugar, sugar spheres, sulfobutylether beta-cyclodextrin, talc, tragacanth, trehalose, and/or xylitol. In one example, the filler can include dicalcium phosphate, calcium phosphate, and combinations thereof. The filler can be present in the formulation at 35 wt % or less. In other examples the filler can be present from about 1 wt % to about 30 wt %, from about 10 wt % to about 30 wt %, from about 20 wt % to about 30 wt %, or from about 25 wt % to about 30 wt %. In some embodiments the fillers can comprise solid particles which are dispersed throughout the formulation.

A further unique property of the formulations presented herein is their ability to dry faster than a comparative formulation applied to a skin surface and dried under the same conditions, despite containing more water. The comparative formulation can include 7 wt % lidocaine, 7 wt % tetracaine, 2 wt % emulsifying agent, 12 wt % polymer, and about 26% water. More specifically, the comparative formulation can include 7 wt % lidocaine, 7 wt % tetracaine, 2 wt % sorbitan monopalmitate, 12 wt % polyvinyl alcohol, 25.94 wt % water, 10 wt % white petrolatum, and 36 wt % dibasic calcium phosphate. In some examples the topical formulation can dry faster while containing about 5 wt % more water, about 6 wt % more water, about 7 wt % more water, about 8 wt % more water, about 9 wt % more water, or about 10 wt % more water than the comparative formulation.

For comparison purposes, in one specific non-limiting example, the local anesthetic(s) in the solid-forming topical formulation can be the same as used in the comparative formulation, the emulsifying agent can be the same as in the comparative formulation, or the polymer can be the same as in the comparative formulation. Thus, for example, one or two of these components can be the same as that used in the solid-forming topical formulation, e.g., the local anesthetics and/or the polymer may be the same, but the emulsifying agent might be different, etc. In another specific non-limiting example, the local anesthetic(s) can be the same as used in the comparative formulation, the emulsifying agent can be the same as in the comparative formulation, and the polymer can be the same as in the comparative formulation, e.g., all three of these components can be the same as that used in the solid-forming topical formulation.

The drying rate can be based on an average drying time of 16 subjects applying and spreading 2.5 grams of the formulations presented herein (or the comparative formulation for comparative purposes) over a 50 $cm^2$ skin surface and allowing the topical formulation (or the comparative formulation) to dry at room temperature. In another example, instead of spreading 2.5 grams for the comparison, 6.5 grams can be spread for the comparison over the same skin surface area (thus, providing a comparative with a thicker application). In one example, the topical formulation can dry, on average, about 1.15 times faster than the comparative formulation dries, e.g., applied using 2.5 gram and/or 6.5 gram. In other examples, the topical formulation can dry, on average, at least 1.10 times faster, at least 1.20 times faster, at least 1.25 times faster, at least 1.30 times faster, or at least 1.35 times faster than the comparative formulation, e.g., applied using 2.5 grams and/or 6.5 grams. In one example, when applied on a skin surface as a 2.5 gram sample at a thickness of 1 mm at ambient/room temperature and relative humidity, the formulation can feel dry to the touch (e.g. the formulation is non-tacky and adheres well to skin) in less than 23 minutes, on average. In another example, when applied on a skin surface as a 6.5 gram sample at a thickness of approximately 1.3 mm at room temperature and relative humidity, the formulation can dry to the touch in less than 43 minutes on average. Other indicators that that a formulation is dry to the touch can include diminished shine, a non-glossy appearance, a change in the surface texture (e.g. a wrinkled appearance), a change in the shade of the color of the formulation, good adhesion to the skin, and/or the like. When determining an "average" drying time or other similar data, average values can be collected using about eight or more samples of a the solid-forming topical formulation applied to eight or more subjects, respectively, for example. In accordance with a specific example of the present disclosure, average data has been collected using 16 subjects. Even larger subject pools can be used to generate reliable "average" dry time data as well.

The formulations presented herein can also exhibit other desirable properties in comparison to the comparative formulation. For example, the topical formulations can be easier to apply and spread as a thin layer than the comparative formulation. The topical formulations can also be easier to remove from the skin than the comparative formulation. In one example, the topical formulations presented herein can dry to a cohesive film that can be removed as a single large piece or two to three large pieces. The cohesive film can be removed without leaving a residue on a skin surface of the subject, thereby eliminating the need to wash a skin surface of the subject following removal. This feature can provide a significant improvement over formulations that require washing off, especially in the clinical setting. This feature can allow the formulation to be used in environments where a sink is not readily available and/or where contamination of surgical instruments is a concern.

In one embodiment, the formulations presented herein can be quick drying solid-forming topical formulations or compositions. For example, the solid-forming topical formulation can include local anesthetic, and polyvinyl alcohol in an amount of more than 12% w/w based on total weight of the topical formulation. The formulation can have a drying time less than about 43 minutes on average when the topical formulation is applied as a 6.5 gram sample at a thickness of less than 2 mm at ambient conditions on human subjects. In one specific example, the formulation can be easily removed and can have a viscosity less than 1,500,000 cps at a temperature of about 25° C. and relative humidity of about 38-45° C., By "easily removed," this can include examples where the formulation forms a solid on the skin and can be removed as one large piece, or in two or three large pieces, for example. In another example, the formulation, after some dying, can exhibit improved film strength over a comparative formulation, and/or improved peelability over a comparative formulation. The term "improved" can include film strengths and/or peelability that provide a better user experience when removing the dried or drying film from the skin. "Improved" properties may be relate to film cohesiveness and/or adhesion properties with respect to the skin surface, for example. In still another example, the formulation can further include water in an amount of more than 26% w/w based on total weight of the topical formulation. Thus, with respect to this particular formulation as well as other solid-forming topical formulation prepared in accordance with principles of the present disclosure, in certain examples, the formulation can be easier to apply and spread in a thin layer, e.g., from 1 mm to 1.5 mm, than a comparative formulation comprising 7 wt % lidocaine, 7 wt % tetracaine, 2 wt % emulsifying agent, 12 wt % polymer and about 26 wt % water.

Turning to certain specific examples that relate the present disclosure, a solid-forming topical formulation can include lidocaine, tetracaine, an emulsifying agent, polyvinyl alcohol, and water. The solid-forming topical formulation can form a cohesive film (upon some amount of drying) that can be removed as one large piece or two to three large pieces. The formulation can be as described herein in accordance with the present disclosure.

In another example, a method of preventing pain can include applying a layer of a topical formulation to a skin surface of a subject and maintaining the layer on the skin surface of the subject for a period of time sufficient to allow the formulation to deliver the local anesthetic to the subject, thereby numbing the skin surface. For superficial dermatological procedures such as dermal filler injection, non-ablative laser facial resurfacing, or pulsed-dye laser therapy, the formulation can be applied to skin for about 20-30 minutes prior to the procedure. For superficial dermatological procedures such as laser-assisted tattoo removal, the formulation can be applied to skin about 60 minutes prior to the procedure. The formulation in this method can be as described herein in accordance with the present disclosure.

In another example, a method of treating pain, e.g., existing pain, can include applying a layer of the topical formulation to a skin surface of a subject and maintaining the layer on the skin surface for a period of time sufficient to allow the formulation to deliver the local anesthetic to a subject, thereby reducing pain. The formulation in this method can be as described herein in accordance with the present disclosure.

In yet another example, a method of preventing pain in a subject prior to a dermatological procedure can include applying a layer of a solid-forming topical formulation including from 4 wt % to 30 wt % of a local anesthetic to a treatment site of a subject, maintaining the layer of the formulation on the treatment site for a period of time sufficient to allow the layer of the formulation to transition from a semi-solid to a cohesive film and to topically deliver the local anesthetic to the treatment site of the subject, and removing the layer of the formulation from the treatment site of the subject by peeling the layer of the formulation off the treatment site. The layer of the formulation can be formulated to convert into a coherent film that can be removed as a single piece or as two to three large pieces and does not leave a residue on a surface of a treatment site. The layer of the formulation can exclude a backing layer, a backing film, or other support substrates and may not require further treatment to transition from the semi-solid to the cohesive film. The formulation can dry at least 1.10 times faster, or at least 1.25 times faster, than a comparative formulation having less water. The comparative formulation can include 7 wt % lidocaine, 7 wt % tetracaine, 2 wt % emulsifying agent, 12 wt % polymer and about 26 wt % water. In one example, this method can be used prior to a dermatological procedure. Exemplary dermatological procedures include but are not limited to, dermal filler injection, pulsed dye laser therapy, facial laser resurfacing, laser or other type of hair removal, laser assisted tattoo removal, or combinations thereof.

In one embodiment, the method provides topical pain relief for superficial dermatological procedures such as dermal filler injection, pulsed dye laser therapy, facial laser resurfacing, laser-assisted tattoo removal, and laser hair removal. In another embodiment, the formulations allow for better patient management in a clinical setting. For example, the formulations are easier to apply, dry faster, and are easier to remove thereby allowing effective, efficient preparation of a patient prior to dermatological procedures. The inventive formulations avoid complications associated with current messy formulations that are difficult to apply and leave a residue on the skin. Additional steps to remove residue from the skin can cause procedural delays, require the presence of additional facilities such as a washing station, and can increase the potential for cross-contamination. The inventive formulations form a cohesive film for improved product removal. In addition, the reduction in drying time increases the number of patients that may be treated in a given timeframe. Such improvements provide for shorter clinical visits and better patient experience. The formulation in this method can be as described herein in accordance with the present disclosure.

In yet another example, a method of treating existing pain in a subject can include applying a layer of a solid-forming topical formulation including from 4 wt % to 30 wt % of a local anesthetic to a skin surface of a subject, maintaining the layer of the formulation on the skin surface for a period of time sufficient to allow the layer of the formulation to transition from a semi-solid to a cohesive film and to topically and/or transdermally deliver the local anesthetic to the subject, and removing the layer of the formulation from the skin surface of the subject by peeling the layer of the formulation off the skin surface. The layer of the formulation can be formulated to convert into a coherent film that can be removed as a single piece or as two to three large pieces. The layer of the formulation can exclude a backing layer, a backing film, or other support substrates and may not require further treatment to transition from the semi-solid to the cohesive film. The formulation can dry at least 1.10 times faster, or at least 1.25 times faster, than a comparative formulation having less water. The comparative formulation can include 7 wt % lidocaine, 7 wt % tetracaine, 2 wt % emulsifying agent, 12 wt % polymer and about 26 wt % water. In one example, the subject can be suffering from neuropathic pain, and in yet other examples, the subject can be suffering from musculoskeletal pain, from inflammatory pain, and the like. The formulation in this method can be as described herein in accordance with the present disclosure.

Thus, the formulations of the present disclosure can be for pain control and can be used to prevent pain or to treat a variety of existing pains. Typically, the formulations of the present disclosure can provide pain prevention or relief within about 60 minutes, within about 45 minutes, or even in as short of a time as within about 30 minutes after application to a skin surface. In order for the solid-forming topical formulation to provide pain prevention or relief, it is generally desirable that the formulation remain on the skin surface of the subject for a period of at least about 20 minutes, at least about 15 minutes, or at least about 10 minutes.

When the formulation is being used to treat existing pain the source or underlying cause of the pain can vary. Using neuropathic pain as an example, non-limiting examples of causes of neuropathic pain include diabetic neuropathies and pain associated with surgery, and/or postsurgical/post-traumatic conditions. Once applied, the solid-forming topical formulations of the present disclosure can be left on the skin surface, either as the semi-solid or as the soft cohesive film, for extended periods of time. After sufficient water evaporation, the semi-solid will form a soft cohesive film that can be removed from the skin as a solid. Unlike in the initial state that has more of a thick liquid or pasty consistency that can be removed by simple wiping, the soft cohesive film can be removed as one large piece or two to three large pieces once transformed from the semi-solid to the soft coherent solid or coherent film.

EXAMPLES

The following examples illustrate the embodiments of the disclosure that are presently best known. However, it is to be understood that the following are only exemplary or illustrative of the application of the principles of the present disclosure. Numerous modifications and alternative compositions, methods, and systems may be devised by those skilled in the art without departing from the spirit and scope of the present disclosure, The appended claims are intended to cover such modifications and arrangements. Thus, while the present disclosure has been described above with particularity, the following examples provide further detail in connection with what are presently deemed to be the most practical embodiments of the disclosure.

Example 1—Viscosity Testing of the Formulations

The following outlines the testing procedures for measuring the viscosity of formulations of the present disclosure.
1. The samples to be tested are removed from the refrigerator and allow them to equilibrate to room temperature (about 25° C.) for at least 1 hour before handling.
2. Using a balance, place the empty small sample adapter (13R) on the balance, and press the tare button. Once the adapter has been tared, fill it with sample material to approximately ⅓ of the total weight (about 7 grams). Tap the adapter on a hard surface for several seconds to remove any entrapped air that might be present in the bottom. Continue to fill the sample adapter ⅓ at a time with additional sample material while tapping to remove entrapped air until the sample weight is 20 grams to 21 grams (maximum).
3. Using a balance centrifuge, spin the sample in the adapter for approximately 30 seconds at a high speed (approximately 4000 rpm) in order to remove any additional air bubbles within the sample.
4. After centrifuging, add additional sample material (about 1 gram) to obtain a final sample weight that is 21 grams to 22 grams. Record the sample weight (in grams).

5. Set the temperature controller on the viscometer (Brookfield RVDV II) to 23±2° C. Equilibrate the sample in the small sample adapter. Using a thermometer, insert the probe no more than 1 cm into the center of the sample, away from the adapter walls.
6. The sample is now ready to be tested on the viscometer. Insert the sample adapter into the sample adapter holder, align the groove, and lock into place. Remove the back holder supporting the sample adapter by unscrewing the nut located behind the spindle coupling nut module. Align the spindle coupling link with the viscometer coupling nut, and rotate the spindle clockwise. Replace the back holder, submerging the spindle in the middle of the sample holder at the same time. Avoid sample perturbation as much as possible. Screw the nut maintaining the back adapter behind the spindle coupling nut module. The spindle should be immersed in the sample up to the middle of the shaft indentation for the viscosity measurement. Failure to immerse the spindle up to the middle of the shaft indentation could result in a faulty viscosity reading.
7. Once the spindle is firmly in place, press the "SET SPEED" key once, and use the t or j arrows to set the spindle speed to 4.0 rpm. Press the "SET SPEED" key again. Once the proper speed (4.0 rpm) and spindle (7) are shown in the display, set the timer to countdown from 2 minutes.
8. Simultaneously start the timer and press the "MOTOR ON/OFF" key to begin the viscosity measurement. Allow the reading to equilibrate for 2 minutes before recording the viscosity reading and % torque value.
9. If the reading is out of the viscometer's range (% torque reading>100.0%), the cp and torque reading will display EEEE. At this point, turn off the motor, change the speed to the next lowest setting, and re-start the timer for 2 minutes. Turn the motor and timer on simultaneously, and allow the reading to equilibrate for 2 minutes before recording the torque and viscosity values. If the torque and viscosity are still out-of-range (EEEE) continue to incrementally reduce the speed, and re-run the sample until % T and viscosity values are in range.
10. After an equilibration time of 2 minutes has elapsed, record the % torque and viscosity values. Press the motor key off. At this point, unlock and carefully remove the sample adapter from the sample adapter holder. Remove the spindle from the viscometer by holding the viscometer coupling nut and rotating the spindle counter clockwise.
11. Remove the excess sample material from the spindle. The remaining sample in the sample adapter can be placed in the waste container.

Example 2

The total water content of the formulation is significant from the standpoint of chemical stability. It has been shown that in aqueous solutions tetracaine hydrolyzes to 4-butylaminobenzoic acid (4-BABA) and 2-dimethylaminoethanol (DMAE). Thus, degradation products in the formulation should be minimized in order to ensure optimal potency and purity of the formulation. Studies of various formulations (see Table 1 below) have shown that the levels of 4-BABA in the formulation correlate to the total water content in the formulation. In the sense that it is desirable to maintain levels of 4-BABA below 3% after 24 months of storage at 5° C. (shelf-life), for example, it would be desirable to ensure total water content remains below ~50%.

TABLE 1

| Formulation | 1 | 2 | 3 | 4 | 5 |
|---|---|---|---|---|---|
| Water Content | 29.54% | 31.94% | 42.82% | 48.88% | 51.87% |
| 4-BABA level after 12 months storage at 5° C. | 0.75% | 0.82% | 1.09% | 1.42% | 1.50% |
| Projected 4-BABA level after 24 months storage at 5° C. | 150% | 1.64% | 2.18% | 2.84% | 3.00% |
| Ingredients | Wt % | Wt % | Wt % | Wt % | Wt % |
| Lidocaine (base) | 7.00% | 7.00% | 7.00% | 7.00% | 7.00% |
| Tetracaine (base) | 7.00% | 7.00% | 7.00% | 7.00% | 7.00% |
| Purified Water | 29.54% | 31.94% | 42.82% | 48.88% | 51.87% |
| Dicalcium Phosphate | 32.40% | 30.00% | — | — | — |
| Polyvinyl Alcohol | 12.00% | 12.00% | 19.77% | 27.00% | 24.00% |
| White Petrolatum | 10.00% | 10.00% | — | 8.00% | 8.00% |
| Span 40 (Sorbitan Monopalmitate) | 2.00% | 2.00% | 3.30% | 2.00% | 2.00% |
| Methylparaben | 0.05% | 0.05% | 0.09% | 0.10% | 0.10% |
| Propylparaben | 0.01% | 0.01% | 0.02% | 0.02% | 0.03% |
| Corn Starch | — | — | 20.00% | — | — |
| Total | 100% | 100% | 100% | 100% | 100% |

Example 3

Since the formulations herein may be stored in refrigerated conditions, the impact of freezing or cycling temperatures (freeze-thaw) on the formulations is considered. Freeze-thaw cycles may cause the PVA molecules in the formulations to crosslink, resulting in a dramatic increase in viscosity which may make the formulation difficult to spread on skin or even remove from an application tube. A series of cycling (freeze-thaw) studies was performed on several formulations in order to assess the impact of exposure to multiple "freeze-thaw" cycles. One freeze-thaw cycle is defined as exposure to freezing conditions (e.g., −18° C. to 22° C.) for 48 hours followed by exposure to room temperature thawing conditions (e.g., about 25° C.) for 48 hours. A more robust formulation will show less increase in viscosity after exposure to multiple freeze-thaw cycles. It is noted that exceeding the 48 hour time periods for freezing and thawing for a short period of time will typically not impact the test results. Several formulations have been developed and subjected to freeze-thaw cycles. Viscosity at baseline and after each freeze-thaw cycle was measured using the method outlined in Example 1.

The data gathered on the formulations below indicate that the water to PVA weight ratio has an impact on the resistance to freeze/thaw exposures. Formulations having a water:PVA weight ratio greater than 2.5 demonstrated less pronounced viscosity increases after exposure to multiple freeze/thaw cycles, as shown in the Table 2 below.

TABLE 2

| Formulation | 6 | 7 | 8 | 9 | 10 |
|---|---|---|---|---|---|
| Water/PVA weight ratio | 2.16 | 2.46 | 2.57 | 2.85 | 3.16 |
| | Wt % | Wt % | Wt % | Wt % | Wt % |
| Ingredients | | | | | |
| Lidocaine (base) | 7.00% | 7.00% | 7.00% | 7.00% | 7.00% |
| Tetracaine (base) | 7.00% | 7.00% | 7.00% | 7.00% | 7.00% |
| Purified Water | 25.94% | 29.54% | 35.94% | 39.94% | 37.94% |
| Dicalcium Phosphate | 36.00% | 32.40% | 27.00% | 18.00% | 24.00% |

TABLE 2-continued

| | | | | | |
|---|---|---|---|---|---|
| Polyvinyl Alcohol | 12.00% | 12.00% | 14.00% | 14.00% | 12.00% |
| White Petrolatum | 10.00% | 10.00% | 5.00% | 10.00% | 10.00% |
| Span 40 (Sorbitan Monopalmitate) | 2.00% | 2.00% | — | — | 2.00% |
| Span 60 Sorbitan Monostearate) | — | — | 4.00% | 4.00% | — |
| Methylparaben | 0.05% | 0.05% | 0.05% | 0.05% | 0.05% |
| Propylparaben | 0.01% | 0.01% | 0.01% | 0.01% | 0.01% |
| Total | 100% | 100% | 100% | 100% | 100% |
| Initial Viscosity (cP) | 454,500 | 146,000 | 122,500 | 79,500 | 47,800 |
| Freeze/Thaw Viscosity Results (cP) | | | | | |
| 1 cycle | 7,200,000 | 436,500 | 170,000 | 94,500 | 29,440 |
| 2 cycles | >8,000,000 | 427,000 | 226,500 | 114,000 | 29,160 |
| 3 cycles | >8,000,000 | 1,150,000 | 210,000 | 146,000 | 33,080 |
| 4 cycles | >8,000,000 | 2,385,000 | 227,500 | 87,000 | 46,400 |
| 5 cycles | >8,000,000 | 3,310,000 | 333,000 | 137,500 | 38,000 |
| Freeze/Thaw Viscosity Increase | | | | | |
| 1 cycle | 16 | 3 | 1 | 1 | 1 |
| 2 cycles | >18 | 3 | 2 | 1 | 1 |
| 3 cycles | >18 | 8 | 2 | 2 | 1 |
| 4 cycles | >18 | 16 | 2 | 1 | 1 |
| 5 cycles | >18 | 23 | 3 | 2 | 1 |

Example 4

Two solid-forming topical formulations were made and their compositions are listed in Table 3 below. The formulations are identical except Formulation 11 used Span 40 (Sobitan Monopalmitate) as emulsifying agent and Formulation 12 used Span 60 (Sorbitan Monostearate). After about three months, Formulation 11 showed significantly more phase separation than Formulation 12.

TABLE 3

| Formulation<br>Ingredients | 11<br>Wt % | 12<br>Wt % |
|---|---|---|
| Lidocaine | 7.00% | 7.00% |
| Tetracaine | 7.00% | 7.00% |
| Purified Water | 35.94% | 35.94% |
| Dicalcium Phosphate | 27.00% | 27.00% |
| Polyvinyl Alcohol | 14.00% | 14.00% |
| White Petrolatum | 5.00% | 5.00% |
| Span 40 (Sobitan Monooalmitate) | 4.00% | — |
| Span 60 (Sorbitan Monostearate) | — | 4.00% |
| Methyiparaben | 0.05% | 0.05% |
| Propylparaben | 0.01% | 0.01% |
| Total | 100% | 100% |
| Initial Viscosity (cP) | 132,000 | 122,500 |
| Water/PVA weight ratio | 2.57 | 2.57 |

Example 5

For comparison, two different solid-forming topical formulations were formulated and applied to the forearms of subjects in order to assess the application properties, drying times, and removal characteristics of the formulations, as well as the ability of the formulations to prevent pain. The formulations tested are provided in Table 4 below.

TABLE 4

| Formulation Ingredients | 13 Wt % | 14 Wt % |
|---|---|---|
| Lidocaine | 7.00% | 7.00% |
| Tetracaine | 7.00% | 7.00% |
| Purified Water | 25.94% | 35.94% |
| Dicalcium Phosphate | 36.00% | 27.00% |
| Polyvinyl Alcohol | 12.00% | 14.00% |
| White Petrolatum | 10.00% | 5.00% |
| Span 40 (Sobitan Monopalmitate) | 2.00% | — |
| Span 60 (Sorbitan Monostearate) | — | 4.00% |
| Methylparaben | 0.05% | 0.05% |
| Propylparaben | 0.01% | 0.01% |
| Water/PVA weight ratio | 2.16 | 2.57 |

More specifically, sixteen (16) subjects participated in a study where the forearms of each subject was cleaned with an alcohol prep pad (70% isopropyl alcohol), and two 50 $cm^2$ areas were measured and marked on each forearm, for a total of four 50 $cm^2$ areas per subject, 2 on each forearm (64 total). Formulations 13 or 14 were each applied within marked 50 $cm^2$ surface areas at two different thicknesses each. The 2.5 gram doses were applied at about 1 mm thick (the entire 50 $cm^2$ surface area could not be covered using the 2.5 gram dose at 1 mm of thickness) on one arm. The 6.5 gram doses were applied at from 1-2 mm of thickness on the other arm. The formulations were applied and allowed to dry under ambient/room conditions, e.g., temperature from 22° C. to 23° C. and relative humidity from 38% to 45%. The subjects were directed to visually monitor the time required for the surface of each application to become dry to the touch. Then, at 30 minutes of dry time for the 2.5 gram dose, and at 60 minutes of dry time for the 6.5 gram dose, the formulations were removed or were attempted to be removed by peeling the formulations off from the skin as a single piece or two or three large pieces. The application site was evaluated for redness or irritation.

OBSERVATIONS

Formulations 13 and 14 were easy to expel from the containers and apply to the application sites. Formulation 13 was slightly thicker than formulation 14. All of the applications remained well-adhered during the application period. No edge lift or product migration was observed.

The 2.5 gram dose dried to the touch for Formulation 13 on average within 23 minutes (9-32 minutes). On the other hand, the 2.5 gram dose for Formulation 14 dried to the touch, on average, within 17 minutes (12-22 minutes). The 6.5 gram dose dried to the touch for Formulation 13 within 43 minutes (14-64 minutes) on average. On the other hand, the 6.5 gram dose of Formulation 14 dried to the touch within 25 minutes (15-40 minutes) on average. Thus, Formulation 13 took longer to dry than Formulation 14, despite Formulation 13 incorporating 10 wt % less water.

Figure 2:
FIG. 2 pictorially illustrates the removal of a 6.5 g dose of Formulation 13 applied on the forearm of a test subject in accordance with an example of the present disclosure.
Figure 3:
FIG. 3 pictorially illustrates the removal of a 2.5 g dose of Formulation 14 applied on the forearm of a test subject in accordance with an example of the present disclosure.
Figure 4:
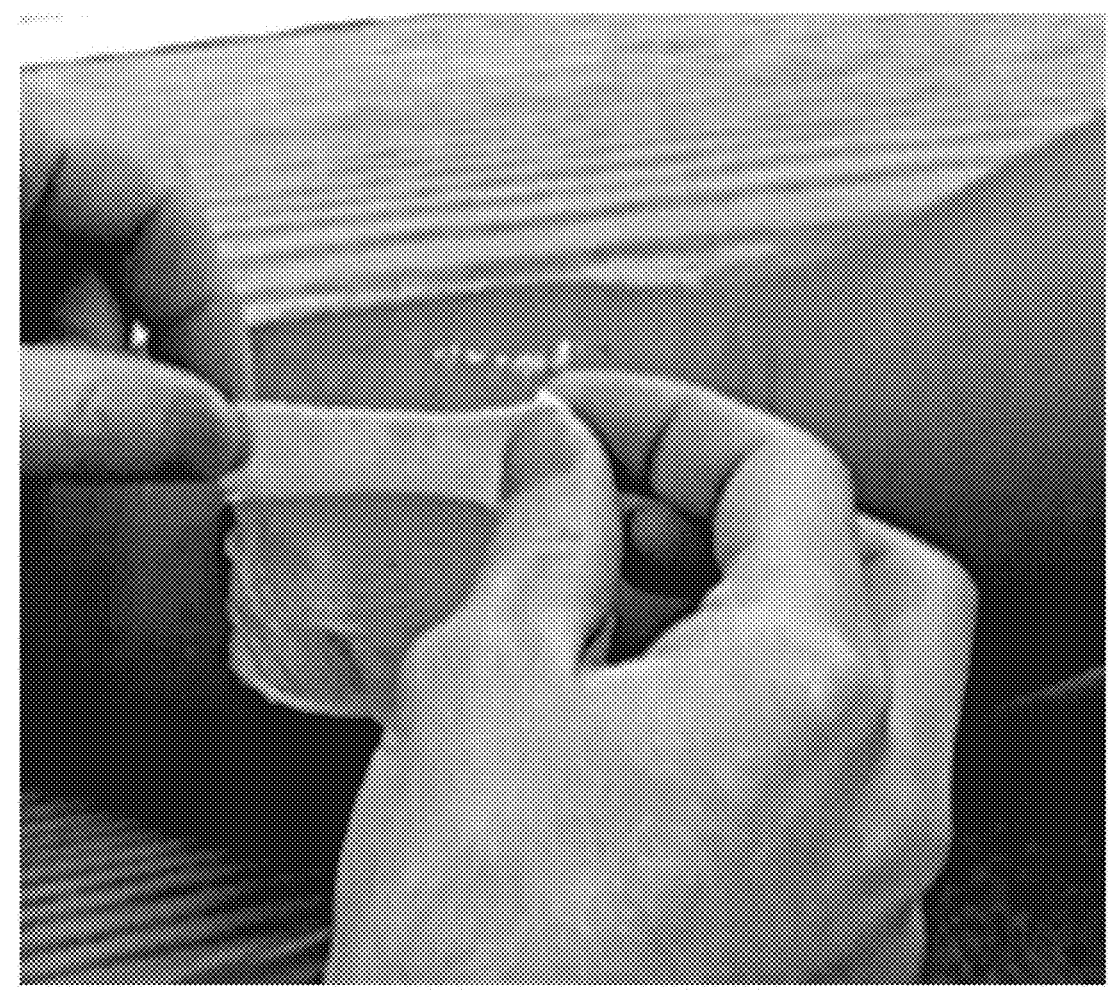
FIG. 4 pictorially illustrates the removal of a 6.5 g dose of Formulation 14 applied on the forearm of a test subject in accordance with an example of the present disclosure.

The most noticeable differences between the formulations occurred during removal at 30 minutes (2.5 gram samples) and at 60 minutes (6.5 gram samples). For example, the 2.5 gram dose of Formulation 13 was not completely dry and peeling the formulation off from the skin was difficult. The formulation did not peel and came off in several small clumps and could be rubbed backwards onto itself as shown in FIG. 1. The 6.5 gram dose of Formulation 13 could be removed in several (more than 3) small pieces and clumps as shown in FIG. 2. This formulation also left a residue that had to be wiped or washed off. On the other hand, both doses (2.5 grams and 6.5 grams) of Formulation 14 were easier and quicker to remove than the removal of both doses for Formulation 13. Formulation 14 could be peeled off the skin in one or as two to three large pieces and did not leave or left minimal amounts of a residue as can be seen in FIG. 3 (2.5 g. sample) and FIG. 4 (6.5 g. sample).

Each of subjects subjectively scored the Formulations for ease of removal with 1 (strongly disagree) being the lowest score and 5 (strongly agree) being the highest score. The scores were averaged for each dose and each formulation. The average scores for the 2.5 gram dose and the 6.5 gram dose of Formulation 13 were 1.81 and 1.75, respectively. The average scores for the 2.5 gram dose and the 6.5 gram dose of Formulation 14 were 4.31 and 4.50, respectively. Other observations included the possibility of removing/peeling the product as a film. Using the same scale and averaging as noted above, the average scores for removing/peeling the product for the 2.5 gram dose and the 6.5 gram dose of Formulation 13 were 1.25 and 1.38, respectively. The average scores for the 2.5 gram dose and the 6.5 gram dose of Formulation 14 were 4.56 and 4.88, respectively. In terms of peeling the product off in large pieces, using the same scale and averaging as noted above, the average scores for the 2.5 gram dose and the 6.5 gram dose of Formulation 13 were 1.25 and 1.25, respectively. The average scores for the 2.5 gram dose and the 6.5 gram dose of Formulation 14 were 4.56 and 4.94, respectively. Regarding how quickly the product could be removed, using the same scale and averaging as noted above, the average scores for the 2.5 gram dose and the 6.5 gram dose of Formulation 13 were 1.75 and 1.69, respectively. The average scores for the 2.5 gram dose and the 6.5 gram dose of Formulation 14 were 4.19 and 4.50, respectively. Whether the product left a residue was also observed. Using the same scale and averaging as noted above, the average scores for visible residue on the skin for the 2.5 gram dose and the 6.5 gram dose of Formulation 13 were 4.75 and 4.94, respectively. The average scores for the 2.5 gram dose and the 6.5 gram dose of Formulation 14 were 2.44 and 2.31, respectively.

While the invention has been described with reference to certain embodiments, those skilled in the art will appreciate that various modifications, changes, omissions, and substitutions can be made without departing from the spirit of the disclosure. R is therefore intended that the invention be limited only by the scope of the appended claims.

What is claimed is:

1. A method of applying a solid forming local anesthetic formulation, comprising:
   applying a layer of a solid-forming formulation to a skin surface, the solid-forming local anesthetic formulation comprising 4 wt % to 30 wt % of a local anesthetic, 18 wt % to 36 wt % of a filler that is dicalcium phosphate, an emollient, an emulsifying agent, water and a polymer, wherein the polymer is polyvinyl alcohol (PVA) and the solid-forming topical formulation includes a ratio of water to PVA of about 2.16 to about 3.16;
   maintaining the layer of the formulation on the skin surface for a period of time sufficient to allow the layer of the formulation to transition from a semi-solid to a cohesive film and to topically deliver the local anesthetic to the skin surface; and
   removing the layer of the formulation from the skin surface by peeling the layer of the formulation off the skin surface as a single piece or two to three large pieces.

2. The method of claim 1, wherein the layer of the solid-forming local anesthetic formulation and the cohesive film formed therefrom is free of a backing layer, a backing film, or other support substrates.

3. The method of claim 1, wherein the solid-forming topical formulation includes more than 25.94 wt % water.

4. The method of claim 1, wherein the PVA has an average mass ranging from 20,000 to 100,000 Daltons.

5. The method of claim 1, wherein the PVA has a molecular mass ranging from 30,000 to 80,000 Daltons.

6. The method of claim 1, wherein the solid-forming topical formulation includes a ratio of water to PVA of greater than 2.4.

7. The method of claim 1, wherein the solid-forming topical formulation includes a ratio of water to PVA of greater than 2.5.

8. The method of claim 1, wherein the local anesthetic in the formulation comprises lidocaine and tetracaine.

9. The method of claim 8, wherein the lidocaine and tetracaine are each in their base form.

10. The method of claim 8, wherein the lidocaine and tetracaine are in the form of a eutectic mixture at about 2:1 to 1:2 weight ratio.

11. The method of claim 10, wherein the lidocaine and tetracaine are in the form of a eutectic mixture at about 1:1 weight ratio.

12. The method of claim 1, wherein the dicalcium phosphate is present in an amount of 18 to 32.4 wt %.

13. The method of claim 1, wherein the formulation is applied at a thickness of 1 mm or more.

14. The method of claim 1, wherein the formulation remains on the skin surface for a period of at least 20 minutes.

15. The method of claim 1, wherein the formulation remains on the skin surface for a period of at least 30 minutes.

16. The method of claim 1, wherein the formulation remains on the skin surface for a period of at least 45 minutes.

17. The method of claim 1, wherein the formulation is for local anesthesia.

18. The method of claim 1, wherein the emollient is petrolatum.

19. The method of claim 1, wherein the emulsifying agent is sorbitan ester.

20. The method of claim 1, the emollient is petrolatum and the emulsifying agent is sorbitan ester.

21. The method of claim 1, wherein the solid-forming formulation has an initial viscosity from about 40,000 centipoise to about 800,000 centipoise.

* * * * *